United States Patent
Ohishi (10) Patent No.: US 7,267,482 B2
(45) Date of Patent: Sep. 11, 2007

(54) X-RAY DIAGNOSTIC APPARATUS, IMAGING ANGLE DETERMINATION DEVICE, PROGRAM STORAGE MEDIUM, AND METHOD

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/428,957

(22) Filed: Jul. 6, 2006

(65) Prior Publication Data

US 2007/0025508 A1    Feb. 1, 2007

(30) Foreign Application Priority Data

Jul. 15, 2005  (JP) .............................. 2005-207688

(51) Int. Cl.
*A61B 6/08*    (2006.01)

(52) U.S. Cl. .................. 378/205; 378/196; 378/62

(58) Field of Classification Search ............... 378/4, 378/8, 62, 95, 193, 195, 196, 205
See application file for complete search history.

(56) References Cited

FOREIGN PATENT DOCUMENTS

| JP | 2004-20621 | 1/2004 |
|----|------------|--------|
| JP | 2004-329729 | 11/2004 |

*Primary Examiner*—Courtney Thomas
(74) *Attorney, Agent, or Firm*—Oblon, Spivak, McClelland, Maier & Neustadt, P.C.

(57) ABSTRACT

An X-ray diagnostic apparatus includes an X-ray tube, an X-ray detector, a support mechanism which movably supports the X-ray tube and the X-ray detector, a storage unit which stores data of a three-dimensional model associated with a standard blood vessel structure, and a control unit which controls the support mechanism on the basis of the three-dimensional model so as to make an imaging central line between the X-ray tube and the X-ray detector become substantially orthogonal to a blood vessel axis of the three-dimensional model at a designated position.

20 Claims, 7 Drawing Sheets

F I G. 1

F I G. 2

FIG. 3  Whole body 2D model data

FIG. 5  3D model data of coronary arteries

X-RAY DIAGNOSTIC APPARATUS, IMAGING ANGLE DETERMINATION DEVICE, PROGRAM STORAGE MEDIUM, AND METHOD

CROSS-REFERENCE TO RELATED APPLICATIONS

This application is based upon and claims the benefit of priority from prior Japanese Patent Application No. 2005-207688, filed Jul. 15, 2005, the entire contents of which are incorporated herein by reference.

BACKGROUND OF THE INVENTION

1. Field of the Invention

The present invention relates to an X-ray diagnostic apparatus which has a high degree of freedom concerning an imaging angle owing to a mechanism including a C-arm and the like, an imaging angle determination device, a program storage medium, and a method.

2. Description of the Related Art

In diagnosis using an X-ray diagnostic apparatus, and more specifically, in diagnosis of a case of stricture, imaging needs to be performed such that the axial direction of a blood vessel does not become parallel to the depth direction (projection direction) of X-rays. Note that angles of the imaging angles of X-rays which are used for medical treatment and diagnosis are also called working angles. If, for example, imaging is performed while a blood vessel runs along the depth direction, since an X-ray image is a kind of shadowgraph, a projected image of the blood vessel is shorter than the actual blood vessel. This makes it impossible to perform proper measurement. This phenomenon is called shortening. Conventionally, imaging must be repeatedly performed at different angles.

In order to solve this problem, according to the prior art, blood vessels in a patient are imaged from a plurality of directions, and a three-dimensional image of the blood vessels is reconstructed on the basis of the resultant imaging data, thereby identifying a target blood vessel on the reconstructed three-dimensional image.

In order to obtain a three-dimensional image of blood vessels, the following methods are used: a method of using only data obtained in a very small number of directions, i.e., two or three directions, and a method of performing reconstruction on the basis of data obtained by performing imaging in many directions as in an X-ray computed tomography apparatus.

In the former method, it is necessary to associate corresponding positions between frames, and it is difficult to automate this. This operation always requires a doctor or technologist with rich clinical knowledge to perform designation, and hence hinders the flow of examination in some case. The latter method does not require such manual operation. However, complicated preparation is required for special imaging operation in this method, and a long processing time is needed after imaging operation. This may also hinder the flow of examination (see Jpn. Pat. Appln. KOKAI Publication No. 2004-020621).

BRIEF SUMMARY OF THE INVENTION

It is an object of the present invention to set a suitable imaging angle with respect to a blood vessel.

An X-ray diagnostic apparatus according to the present invention comprises an X-ray tube, an X-ray detector, a support mechanism which movably supports the X-ray tube and the X-ray detector, a storage unit which stores data of a three-dimensional model associated with a standard blood vessel structure, and a control unit which controls the support mechanism on the basis of the three-dimensional model so as to make an imaging central line between the X-ray tube and the X-ray detector become substantially orthogonal to a blood vessel axis of the three-dimensional model at a designated position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below with reference to the views of the accompanying drawing. Note that this embodiment will exemplify an X-ray diagnostic apparatus having an imaging angle optimization support function, but may be provided as an imaging angle optimization support device which serves as part of an X-ray diagnostic apparatus. In addition, the embodiment can be provided as a program for causing a computer to implement processing for supporting the optimization of an imaging angle, and a storage medium storing the program.

Figure 1:
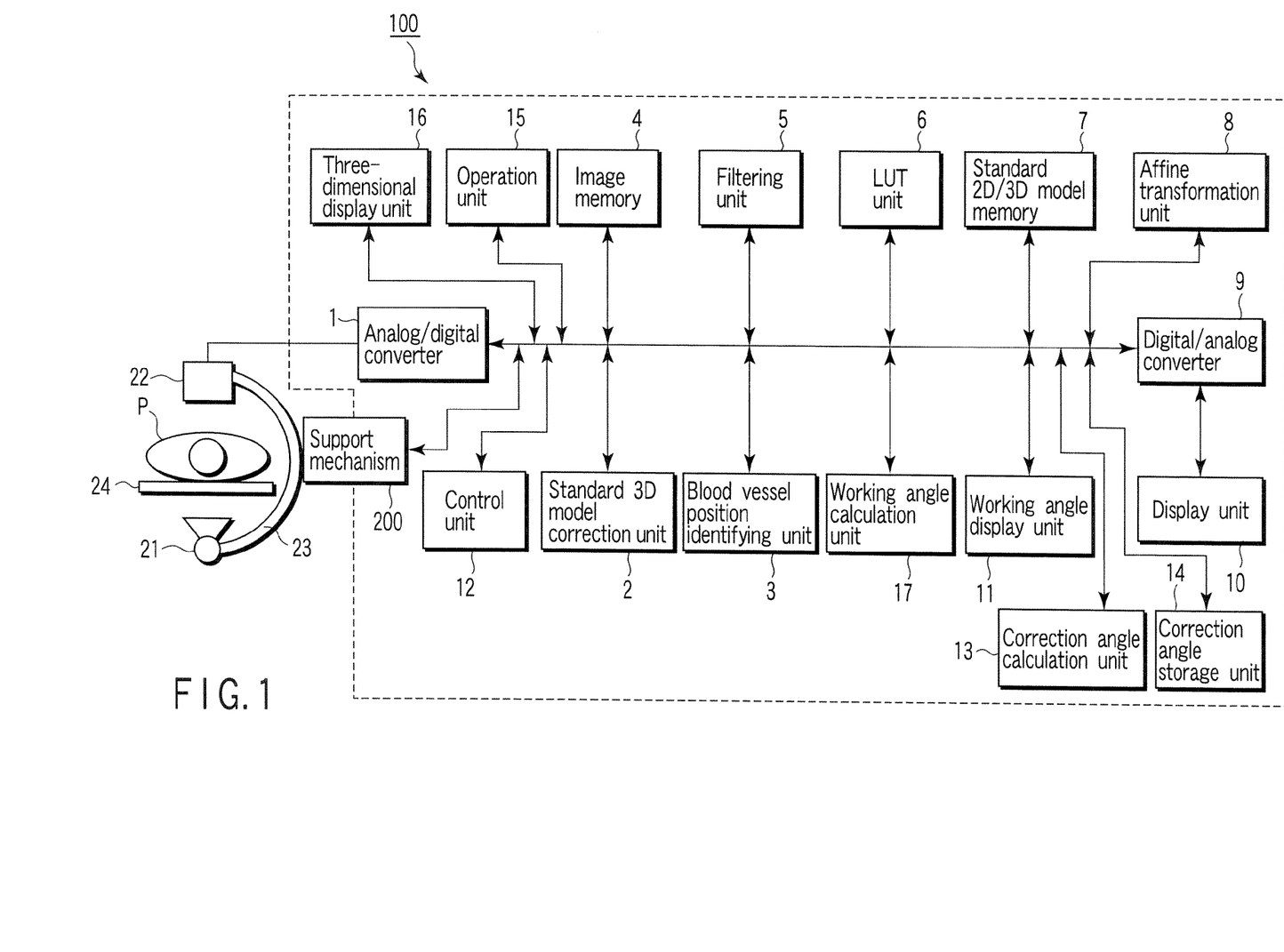
FIG. 1 is a block diagram showing the arrangement of the main part of an X-ray diagnostic apparatus according to an embodiment of the present invention.
Figure 2:
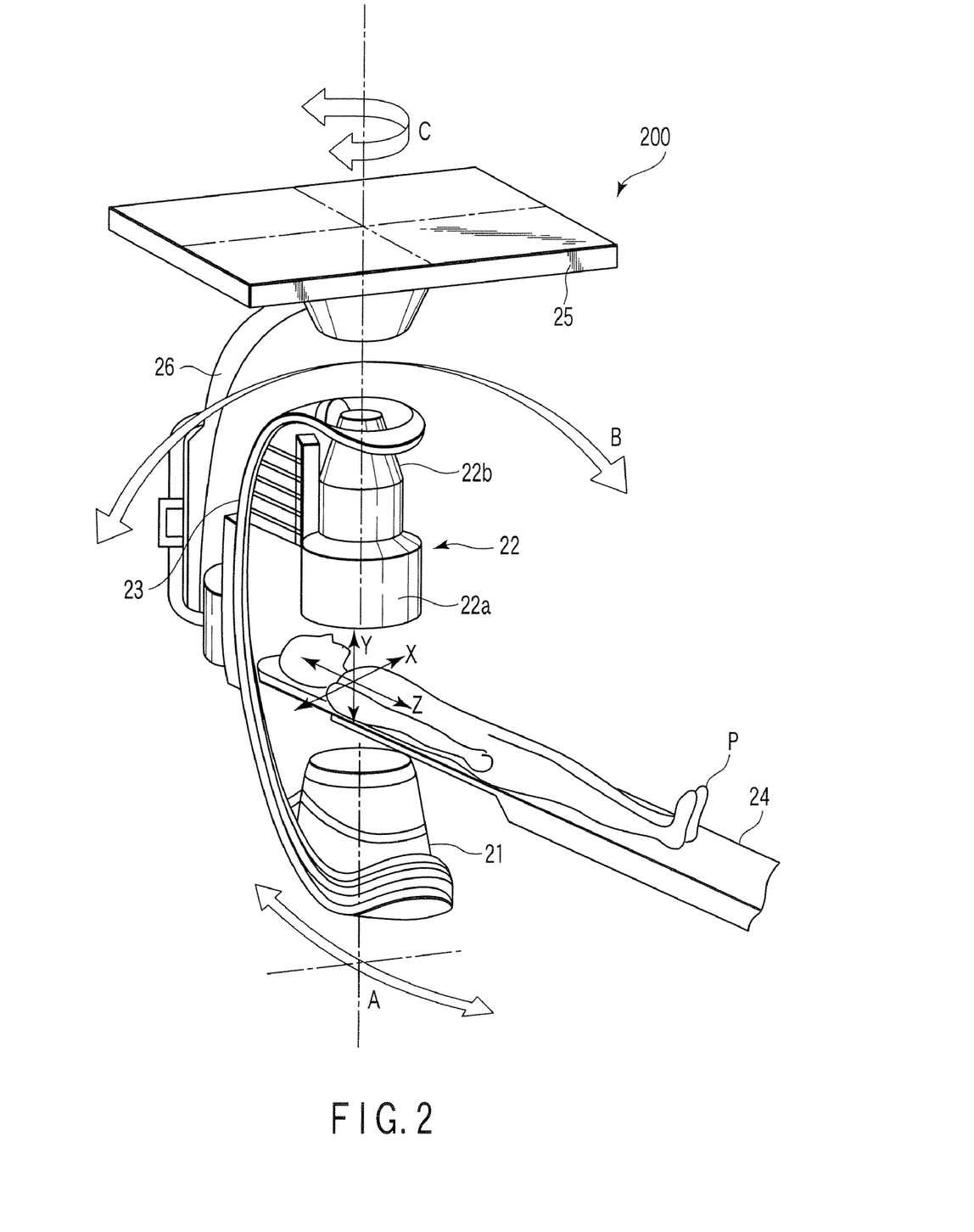
FIG. 2 is an external view of a C-arm mechanism in FIG. 1.

FIG. 1 shows the arrangement of the main part of the X-ray diagnostic apparatus according to this embodiment. An X-ray tube 21 generates X-rays upon reception of a high voltage (tube voltage) and filament current from a high voltage generator (not shown). The X-ray tube 21 is mounted on one end of a C-arm 23. An X-ray detector 22 is mounted on the other end of the C-arm 23. The X-ray detector 22 faces the X-ray tube 21. For example, as shown in FIG. 2, the X-ray detector 22 comprises an image intensifier 22a and a TV camera 22b. The X-ray detector 22 may comprise a flat panel detector (FPD) comprising a two-dimensional array of a plurality of detection elements (pixels) which directly or indirectly convert incident X-rays into electric charges. When imaging is performed, a subject P on a bed 24 is placed between the X-ray tube 21 and the X-ray detector 22.

FIG. 2 shows the outer appearance of a C-arm support mechanism 200. The C-arm 23 is supported from a ceiling base 25 through a suspension arm 26 such that the C-arm can rotate in the directions of arrows A, B, and C with respect to the three orthogonal axes, i.e., the X-, Y-, and Z-axes so as to freely change the imaging angle with respect to the subject P. Note that a straight line passing through the X-ray focal point of the X-ray tube 21 and the detection surface center of the X-ray detector 22 is called an imaging axis. Imaging angles are typically defined as the intersection angles of the imaging axis with respect to three orthogonal X-, Y-, and Z-axes, and are conventionally expressed as the angles of the first oblique (RAO), the second oblique (LAO), the third oblique (LPO), and the fourth oblique (RPO). Typically, the Z-axis is defined as an axis which substantially coincides with the body axis of the subject, the Y-axis, which coincides with the imaging axis with respect to the Z-axis, and the X-axis intersect at an imaging fixed point (isocenter).

Referring back to FIG. 1, a computer 100 is connected to the X-ray detector 22 through an analog/digital converter 1. The computer 100 is provided with, in addition to the analog/digital converter 1, a control unit 12 which is in charge of control of the overall system, imaging sequence control, movement control of the C-arm 23 with respect to the support mechanism 200, and the like, an operation unit 15 including a keyboard, a mouse, and the like, an image memory 4 which stores the data of an image obtained by imaging, a filtering unit 5 which performs high frequency enhancement filtering and the like, an affine transformation unit 8 which performs image enlargement/movement and the like, a lookup table (LUT) 6 which performs tone conversion, an X-ray tube control unit (not shown), a C-arm control unit (not shown), a detector control unit (not shown), and a three-dimensional display unit 16 which performs three-dimensional image display processing. The computer 100 is also provided with a display unit 10 including a display through a digital/analog converter 9.

The computer 100 includes, in addition to the above constituent elements for mainly implementing the general functions described above, a standard 2D/3D model memory 7, blood vessel position identifying unit 3, working angle calculation unit 17, working angle display unit 11, correction angle calculation unit 13, correction angle storage unit 14, and standard 3D model correction unit 2 as constituent elements for mainly implementing an imaging angle optimization support processing function.

Figure 3:
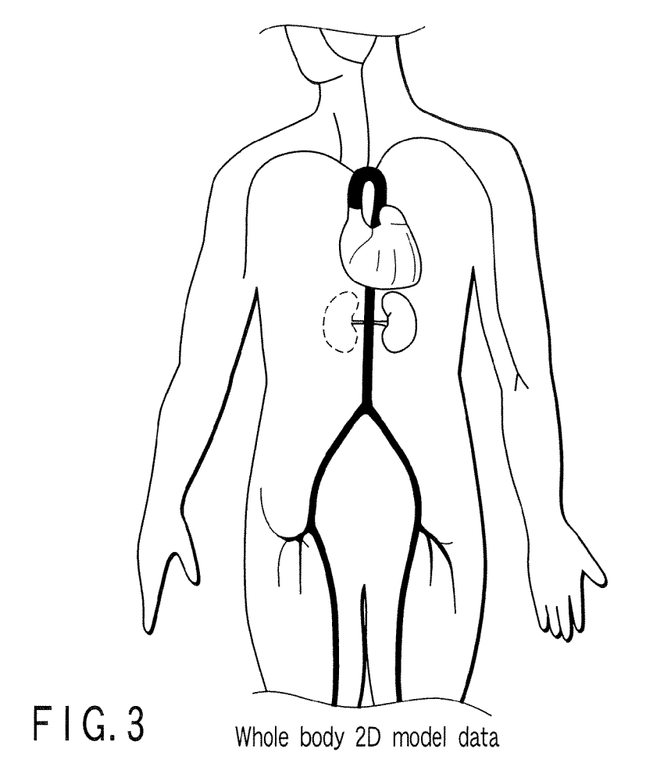
FIG. 3 is a view showing an example of a whole body 2D model stored in a standard 2D/3D model memory in FIG. 1.
Figure 4A:
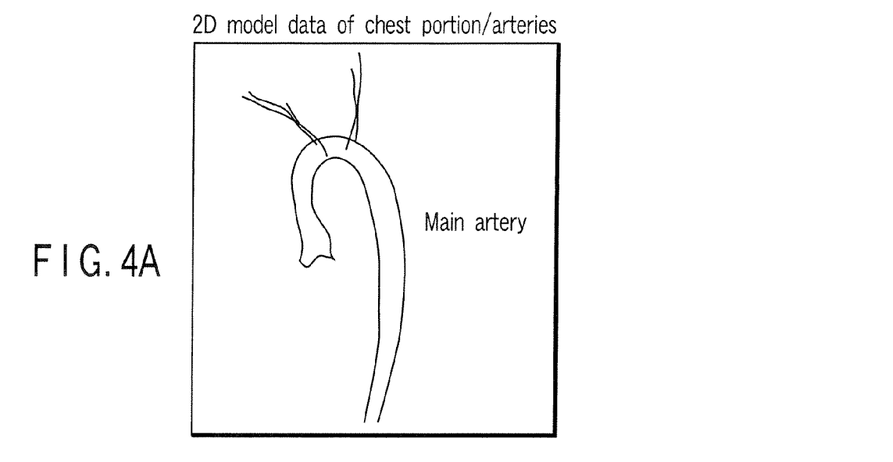
FIGS. 4A to 4C are views showing examples of 2D models associated with a plurality of regions included in a chest portion classification (large classification) and artery classifications (small classifications) which are stored in the standard 2D/3D model memory in FIG. 1.
Figure 4B:
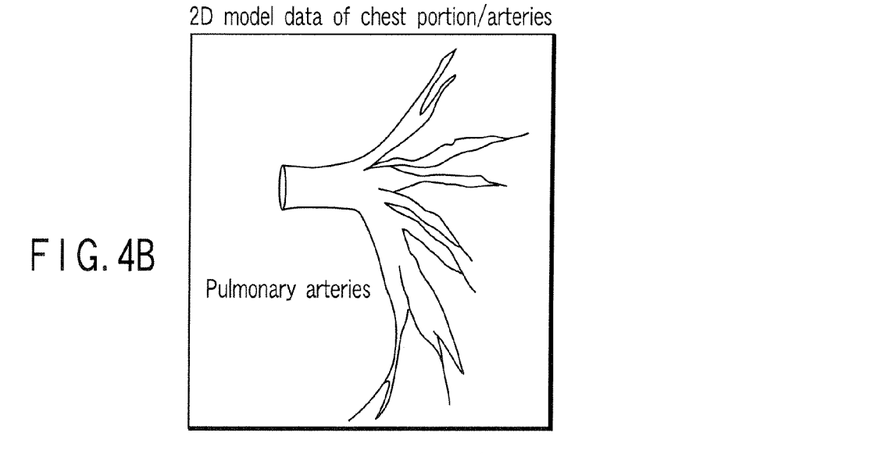
Figure 4C:
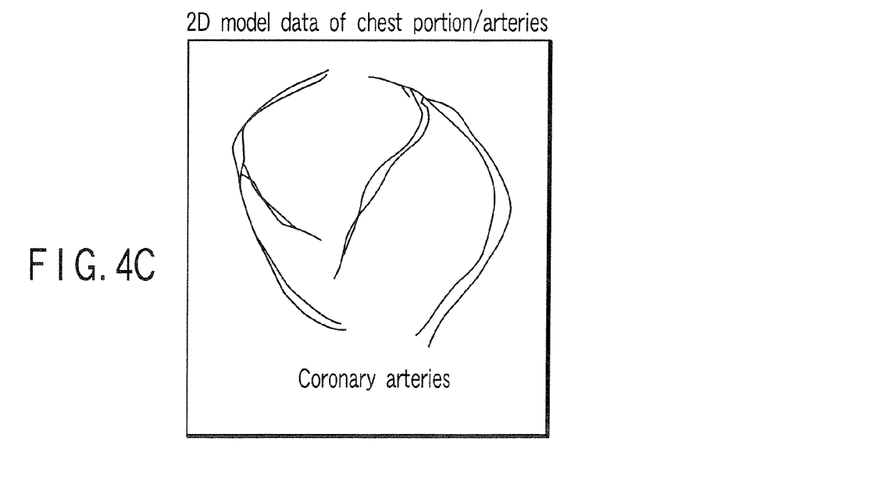
Figure 5:
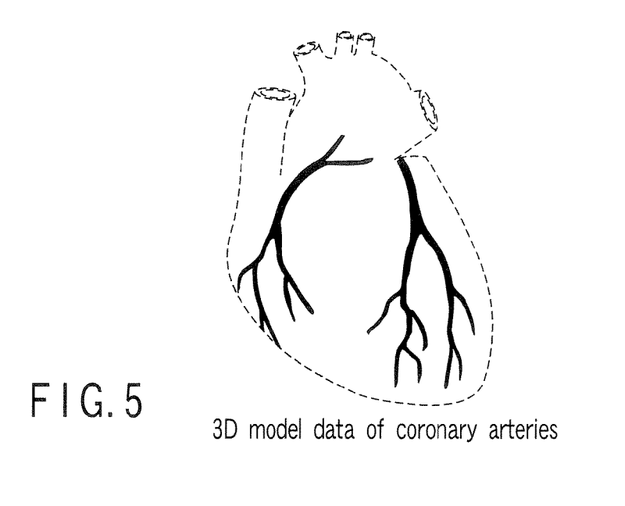
FIG. 5 is a view showing an example of a 3D model of coronary arteries stored in the standard 2D/3D model memory in FIG. 1.

The standard 2D/3D model memory 7 stores the two-dimensional data of an almost whole human body model, the data of a two-dimensional model associated with the typical systematic blood vessels of the human body shown in FIG. 3, the data of a plurality of two-dimensional models associated with blood vessels in a plurality of regions of the human body exemplified in FIGS. 4A, 4B, and 4C, and the data of a plurality of standard three-dimensional models associated with the blood vessel structures of a plurality of regions exemplified in FIG. 5. Typically, standard three-dimensional model data range from three-dimensional data (to be also referred to as volume data) formed by imaging a human body model (phantom) elaborated up to the details of the internal structure by volume scanning such as helical scanning using an X-ray computed tomography apparatus to data associated with a three-dimensional model representing the blood vessel structure in each region extracted by threshold processing or the like. Alternatively, a standard three-dimensional model formed on the basis of data obtained by investigation by a governmental institution or a public institution such as an academic society may be used.

In the data of a plurality of standard three-dimensional models associated with a plurality of blood vessel structures corresponding to a plurality of regions, the names of relatively wide portions of the body, e.g., an abdominal portion, chest portion, and lower limb portion, the names of relatively local regions, e.g., arteries and veins, the names (intrinsic codes) of so-called examination protocols which present and define examination and imaging sequences for the respective examination objects, imaging parameters, and the like, and comments about imaging, e.g., impressions of doctors or imaging technologists are associated with each other. With this association, a plurality of standard three-dimensional models can be roughly classified according to relatively wide portions of the body, and each of the relatively wide portions can be further classified into smaller local regions. In addition, the classified regions can be hierarchically displayed.

Likewise, with regard to a plurality of two-dimensional models associated with blood vessels in a plurality of regions of the human body, the names of relatively wide portions of the body, the names of relatively local regions, the names of examination protocols, and comments about imaging are associated with each other. With this association, a plurality of two-dimensional models can be roughly classified according to relatively wide portions of the body, and each of the relatively wide portions can be further classified into smaller local regions. In addition, the classified regions can be hierarchically displayed.

Figures 8, 9:
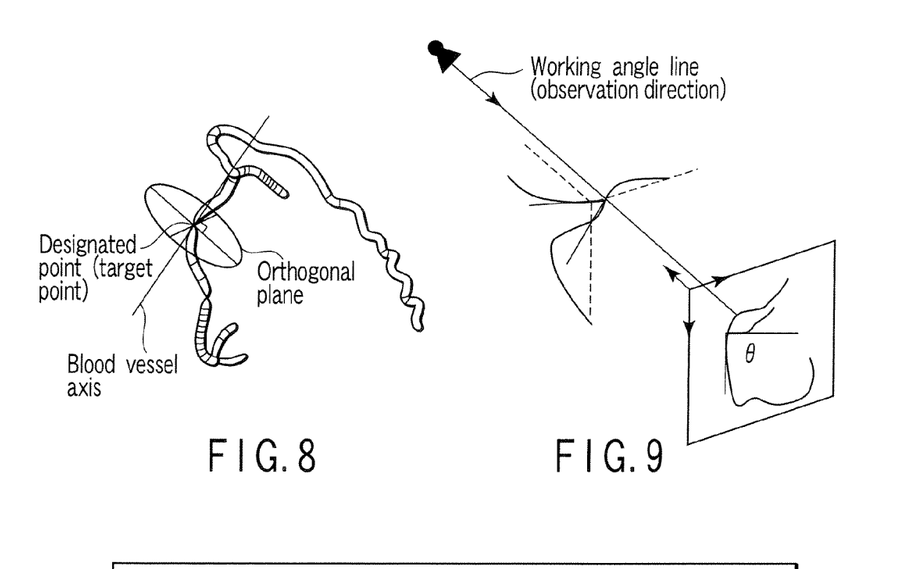
FIG. 8 is a view for supplementary explanation of a plane orthogonal to a blood vessel axis set by a working angle calculation unit in FIG. 1.
FIG. 9 is a view for supplementary explanation of correction angle calculation processing by a correction angle calculation unit in FIG. 1.

The blood vessel position identifying unit 3 identifies the coordinates of a target point on a target blood vessel designated through the operation unit 15 on a displayed standard blood vessel 3D model, and specifies a plane substantially orthogonal to a tangent line to the target blood vessel at the target point or the axis of the blood vessel (see FIG. 8). The blood vessel position identifying unit 3 calculates an arcuated path centered on the target point and having an arbitrary radius which is located on the orthogonal plane and on which the X-ray foal point of the X-ray tube 21 moves. The blood vessel position identifying unit 3 also calculates an arcuated path which is located on the orthogonal plane and on which the center of the effective detection surface of the X-ray detector 22 moves.

Note that the start and end points of an arcuated path are determined under the physical/structural constraints of the support mechanism 200, and the X-ray tube 21 can be placed at any position within the range of the arcuated path. At any position on the arcuated path calculated in this manner, the target blood vessel can be imaged from its side, i.e., a direction in which no shortening occurs, at the target position. Providing this arcuated path makes it possible to support setting work for optimal imaging angles with respect to the blood vessel.

Figure 10:
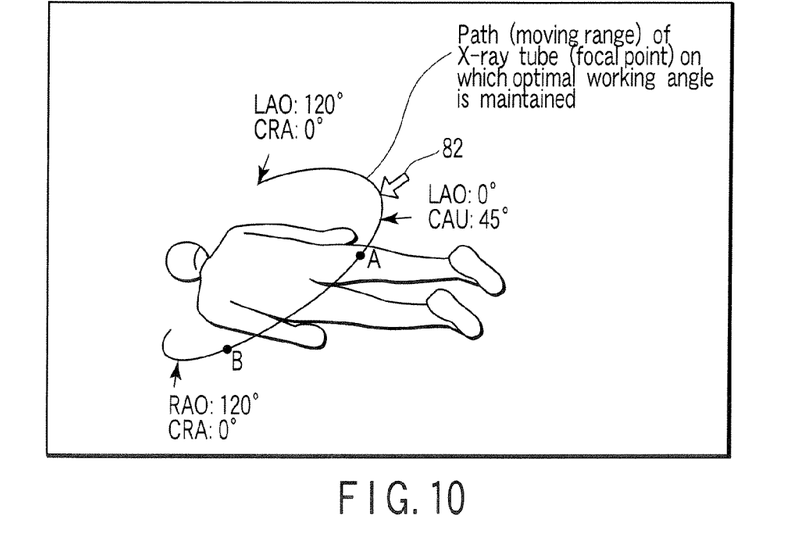
FIG. 10 is a view showing an example of a display window of the moving path of an X-ray focal point and working angles which are displayed by a working angle display unit in FIG. 1.

The working angle calculation unit 17 calculates imaging angles associated with a plurality of representative points exemplified in FIG. 10 on the arcuated path calculated by the blood vessel position identifying unit 3, and calculates an imaging angle associated with a point designated on the arcuated path through the operation unit 15. The working angle display unit 11 performs processing required to display, on the display unit 10, the imaging angles at the representative points calculated by the working angle calculation unit 17 and the designated point as numerical values, together with the arcuated path calculated by the blood vessel position identifying unit 3 and the whole human body model.

The correction angle calculation unit 13, correction angle storage unit 14, and standard 3D model correction unit 2 are provided to calculate the deviation between the position recognized on the anatomical coordinate system of the stored standard three-dimensional model and the position recognized on the coordinate system of the bed on which the subject is actually placed, store the deviation, and perform positional correction of the standard 3D model on the basis of the deviation in calculating blood vessel axis and an orthogonal plane. This angle correction will be described in detail later.

Note that the essence of this embodiment is not limited to the above path calculation. The control unit 12 controls the support mechanism 200 such that an imaging central line connecting the X-ray focal point of the X-ray tube 21 and the center of the effective detection surface of the X-ray detector 22 falls within a substantially orthogonal plane at an arbitrary position (target point) with respect to the blood vessel axis of a three-dimensional model, or controls the support mechanism 200 to limit the movement of the C-arm 23 so as to make it move within the orthogonal plane. This makes it possible to alleviate the problem of shortening.

An imaging angle optimization support sequence according to this embodiment will be described in the situation of catheterization procedures. When examination is started in the X-ray diagnostic apparatus, examination information such as a patient name and a patient ID is input. Such piece of information are either registered online through an HIS (Hospital Information System) or an RIS (Radiology Information System), or manually input to a diagnostic system. The input information includes information indicating the selection of examination protocols, which are, for example, set for each imaging region, e.g., a heart examination protocol, head examination protocol, and abdomen examination protocol.

When various kinds of information necessary for examination are input, examination is started. For example, an instrument such as a catheter or a guide wire is inserted into a blood vessel of a patient and is moved to an examination region. At the examination region, the target blood vessel is imaged from an arbitrary direction, and a target region is checked. In some case, a comment is input before imaging. In general, a blood vessel name is often designated. When a working angle support button as a physical button or an icon on a touch panel on the operation unit 15 is pressed, the two-dimensional model image of the whole body is initially displayed together with segments (broken lines) 31, 32, and 33 of relatively wide portions, e.g., an abdominal portion, chest portion, and lower limb portion, as shown on the left side area exemplified in FIG. 6. When, for example, the chest portion (heart) 31 is selected from the segments through the operation unit 15, buttons 41 and 42 respectively corresponding to, for example, arteries and veins are displayed as small classifications on the lower layer of the chest portion. When the artery button 41, of the buttons 41, and 42, is selected and clicked through the operation unit 15, buttons 51, 52, and 53 as representations of standard two-dimensional models in the memory 7 which respectively correspond to, for example, the main artery, pulmonary arteries, and coronary arteries with the large classification being the heart and the small classification being included in the artery segment.

Figure 6:
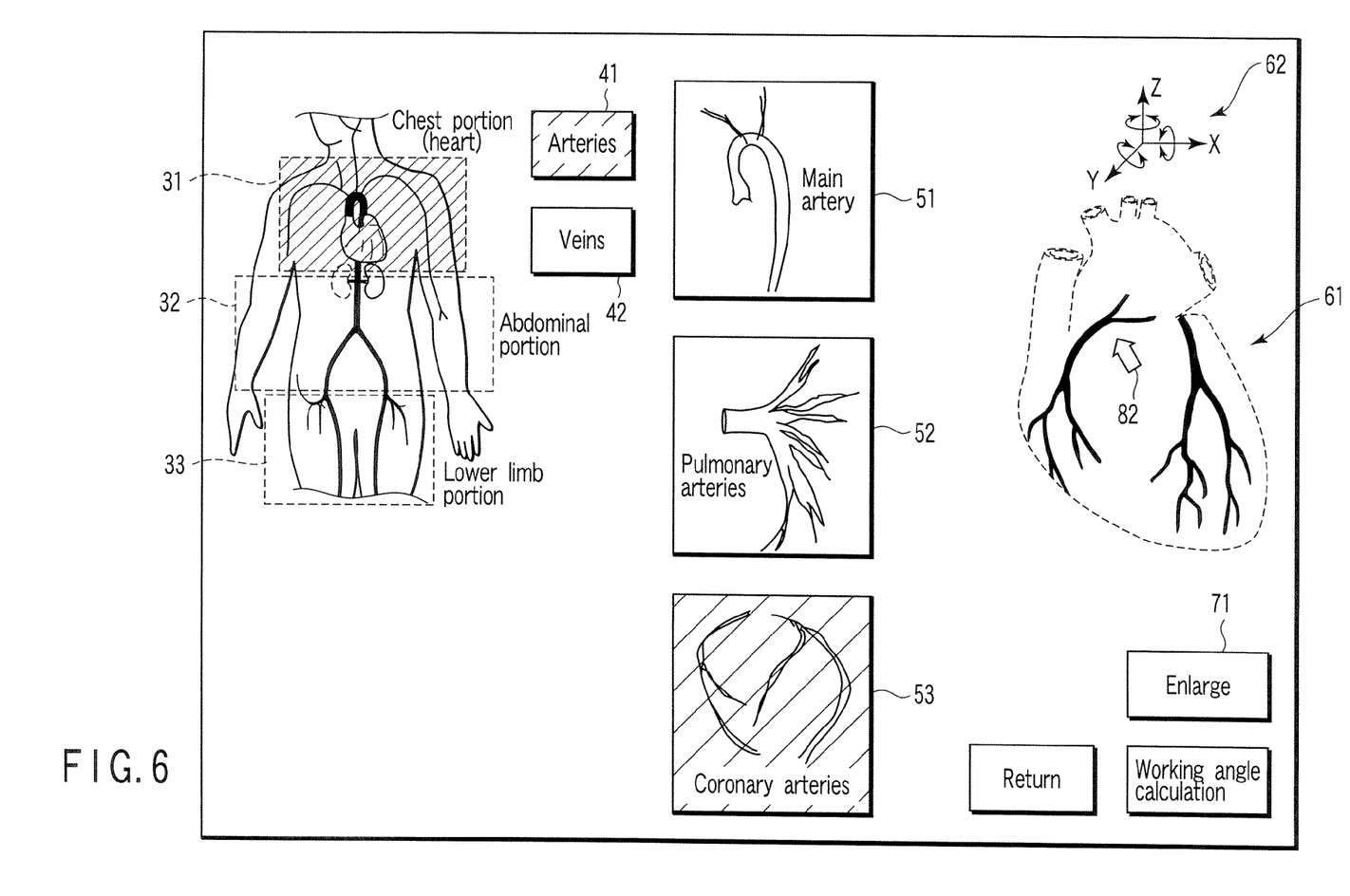
FIG. 6 is a view showing an example of a target point designation window provided by a blood vessel position identifying unit in FIG. 1.
Figure 7:
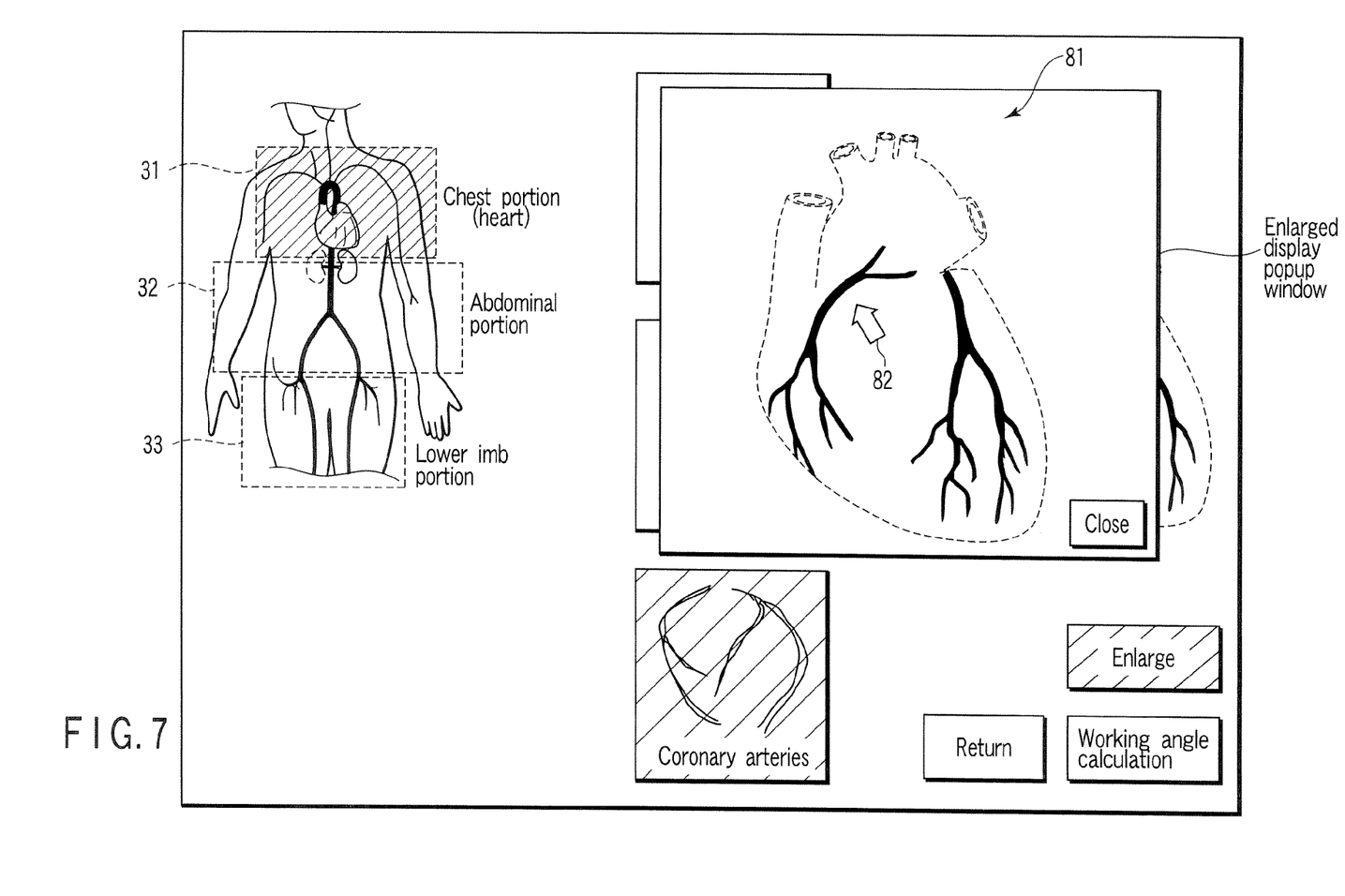
FIG. 7 is a view showing an example of a window for enlargement display which is popped up by clicking an "enlargement" button in FIG. 6.

In this case, when the coronary artery button 53 is designated through the operation unit 15, the data of a three-dimensional model associated with the coronary arteries which is stored in the memory 7 is supplied to the three-dimensional display unit 16. The three-dimensional display unit 16 generates display data from the data of the three-dimensional model by three-dimensional display processing. A three-dimensional image 61 of the coronary arteries is displayed, together with a rotational operation button 62 in accordance with the generated display data. The three-dimensional image 61 of the coronary arteries can be arbitrarily rotated by arbitrarily operating the rotational operation button 62 until the image is set in a proper direction. When an enlargement button 71 is clicked, the three-dimensional display unit 16 generates a three-dimensional image 81 of the coronary arteries with a higher resolution from the data of the three-dimensional model. This image is then displayed in a popup window, as shown in FIG. 7. A target point on a target blood vessel is designated by operating a pointer 82 working with mouse operation on the three-dimensional image 61 or 81. The displayed three-dimensional image of the coronary arteries is displayed initial at the same angle as the observation angle of the X-ray image displayed in the monitor. Thus there is an effect that it becomes easy to compare the X-ray image and three-dimensional image of the coronary arteries, and the target point can be specified accurately.

Note that a level for narrowing down to a blood vessel in a target region may be added. For example, when the coronary arteries are selected, a choice between the right coronary arteries and the left coronary arteries may be displayed. In addition, when the right coronary arteries are designated, the left coronary arteries may disappear, and only a right coronary artery model may be displayed. When the first branch of the right coronary arteries is finally designated, only a blood vessel structure around the first branch may be displayed. The standard three-dimensional model is formed from a hierarchical structure, and a target blood vessel can be easily narrowed down by selecting levels. Note that in selection in the hierarchical structure, a jump can be directly made from the heart to the right coronary arteries, or the left and right coronary arteries may be kept displayed without designation of right or left.

The sequence for manually displaying a target blood vessel sequentially from an upper level has been described. However, for example, a target blood vessel may be automatically displayed in accordance with the examination region and examination purpose contained in an examination protocol.

When a target region is designated on the standard three-dimensional model image 61 or 81, the designated position information is supplied from the control unit 12 to the blood vessel position identifying unit 3, together with the data of a standard three-dimensional model of the corresponding region, i.e., the coronary arteries in this case. The blood vessel position identifying unit 3 identifies the position of the target point on the model coordinate system on the displayed standard three-dimensional model associated with blood vessels in the corresponding region, specifies a tangent line to the target blood vessel or the axis of the blood vessel at the target point, and defines a plane (see FIG. 8) substantially orthogonal to the tangent line or the axis of the blood vessel. The blood vessel position identifying unit 3 calculates an arcuated path which is located on the orthogonal plane, on which the X-ray tube 21 or more accurately the X-ray foal point moves, and has an arbitrary radius centered on the target point. The blood vessel position identifying unit 3 determines the start and end points of an arcuated path under the physical/structural constraints of the support mechanism 200. The information of this arcuated path is supplied to the working angle calculation unit 17.

The working angle calculation unit 17 calculates imaging angles associated with a plurality of representative points on the arcuated path calculated by the blood vessel position identifying unit 3. When a point is designated on the arcuated path through the operation unit 15, an imaging angle associated with the designated point is calculated by the working angle calculation unit 17. As exemplified by FIG. 10, the working angle display unit 11 displays, on the display unit 10, the imaging angles at the representative points calculated by the working angle calculation unit 17 and the designated point as numerical values, together with the arcuated path calculated by the blood vessel position identifying unit 3 and the whole human body model. By processing in the working angle display unit 11, the human body model can be rotated. As the human body model is rotated, the graphic pattern of the arcuated path synchronously rotates. The arc of the path is not a perfect circle but lacks partially. This lacking portion falls within the range in which the X-ray tube 21 of the C-arm 23 cannot be set due to the mechanical constraints of the support mechanism 200. When the pointer 82 is placed on one point on the path, an imaging angle at the point is immediately calculated by the calculation unit 12 and displayed. In this case, the arcuated path has a certain width, and an imaging angle corresponding to the position of the pointer 82 is displayed regardless of any position of the (partly omitted) doughnut-shaped portion at which the pointer 82 is placed.

When, for example, the mouse is double-clicked while the pointer 82 is placed at a given position, information associated with a corresponding imaging angle is supplied to the support mechanism 200 under the control of the control unit 12. When a trigger switch (a switch which moves the support mechanism) on the operation unit 15 is pressed (while a safety check is conducted), the support mechanism 200 provides rotation necessary to attain an imaging angle to the C-arm 23 under the control of the control unit 12. In addition, a three-dimensional model observed from the designated imaging angle is displayed. This allows the operator to know the state of the blood vessel to be observed before the C-arm is moved to the designated angle. The blood vessel which the operator wants to see cannot sometimes be seen at the designated angle when it overlaps another blood vessel depending on the observation angle. This function can prevent such a problem.

Figure 11:
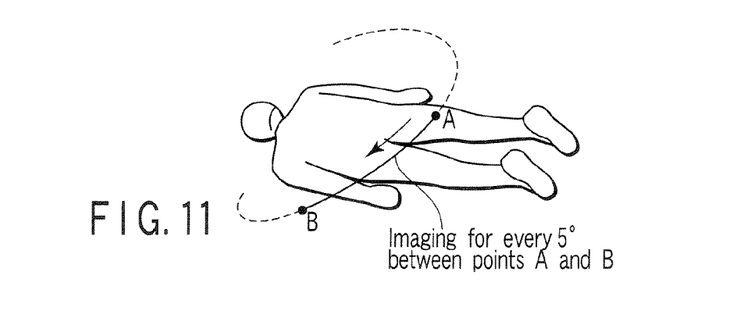
FIG. 11 is a view showing imaging repeated between points A and B in FIG. 10.

When two points A and B are designated on the path, imaging angles at the two points are set in the support mechanism 200. When the trigger switch is pressed, the focal point of the X-ray tube 21 coincides with the position of the point A designated first under the control of the control unit 12. In addition, the C-arm 23 moves until the imaging axis coincides with the imaging angle, and then temporarily stopped (see FIG. 11). When the trigger switch is released and pressed again, the focal point of the X-ray tube 21 continuously or intermittently moves from the point A to the point B along the path under the control of the control unit 12. For example, intermittently injecting a contrast medium with an injection syringe in the meantime makes it possible to specify an angle at which a stricture can be seen more easily in a case of stricture. After the focal point reaches the second designated angle, the C-arm 23 is temporarily stopped. When the trigger switch is released and pressed again, the focal point automatically moves to the first designated angle. In this case, if a rotational imaging program (rotation DA (Digital Angiography), rotational DSA (Digital Subtraction Angiography), or the like) has been selected as an imaging program, an imaging start angle and an imaging end angle are set in the memory when two points are designated.

Although the above description has exemplified the arrangement including the whole body model as a standard 3D model, the embodiment may use an arrangement including a standard 3D model of only a partial area such as the heart or only blood vessels in a portion of the body, e.g., coronary arteries.

In practice, although, for example, the position and direction of the heart on a standard model do not greatly deviate from the position and direction of the heart as a region of a subject to be examined on the bed coordinate system, they do not perfectly match. The deviation between a position recognized on the anatomical coordinate system of the stored standard three-dimensional model and a position recognized on the coordinate system of the bed on which a subject to be actually examined is placed is calculated and stored, and the position of the standard 3D model is corrected in calculation of a blood vessel axis or orthogonal plane on the basis of the deviation. The individual difference in blood vessel running of coronary arteries is not large, and most of the individual differences lie in the inclinations of the whole hearts, and more particularly in positional shifts due to inclinations caused by rotation about the body axes. In such a case, working angle designation can be performed more accurately by correcting the inclination (individual difference) by rotation. Such correction methods include a manual method and an automatic method.

According to the manual method, for example, an area including the heart is imaged with X-rays from a given imaging angle, and a standard three-dimensional model is rotated so as to be seen at an angle similar to the angle of the heart on the image. When they almost match, an angle synchronization switch of the operation unit 15 is pressed. The correction angle calculation unit 13 calculates correction angles for the X-, Y-, and Z-axes which are required to match an imaging angle on the coordinate system on which standard three-dimensional model data are defined with an imaging angle in imaging operation. The standard 3D model correction unit 2 generates a correction rotation matrix corresponding to the calculated correction angle, and performs coordinate transformation of the standard 3D model data by using the correction rotation matrix, thereby correcting the above deviation. Note that the calculated correction angles for the X-, Y-, and Z-axes or the data associate with the correction rotation matrix are stored in the correction angle storage unit 14 in association with information such as patient IDs for identifying subjects to be examined.

When similar examination is to be performed for the same patient, angle correction can be omitted.

According to the automatic correction angle calculation method, as exemplified in FIG. 9, for example, an image obtained by imaging is replayed to display the first branch of a blood vessel, and an angle $\theta^0$ of the first branch is calculated. A standard 3D model is then projected at the same angle as that of the image obtained by imaging and with the same SID (the distance between the X-ray tube and the detector), and an angle $\theta$ of the projected first branch is compared with the angle $\theta^0$. If the angles $\theta^0$ and $\theta$ do not coincide with each other, the standard 3D model is rotated about the body axis through an arbitrary angle $\Delta\theta$ to calculate an angle $\theta^1$ of the first branch. The model is then rotated through an arbitrary angle $-\Delta\theta$ to calculate an angle $\theta^{-1}$ of the first branch. Absolute values $E(\theta^{-1})$, $E(\theta^0)$, and $E(\theta^1)$ of the errors between $\theta$ and $\theta^{1-}$, $\theta^0$, and $\theta^1$ are compared. If $E(\theta^{-1})>E(\theta^0)>E(\theta^1)$, the standard 3D model is rotated about the body axis through an arbitrary angle $2\Delta\theta$, and $E(\theta^2)$ and $E(\theta^1)$ are compared with each other. If the comparison result is opposite, the standard 3D model is rotated about the body axis through an arbitrary angle $-2\Delta\theta$, and $E(\theta^{-2})$ and $E(\theta^{-1})$ are compared with each other. Search operation is sequentially repeated in this manner to obtain a point at which $E(\theta^M)$ is minimized. A rotation angle for setting $\theta^M$ is calculated as a correction angle. Note that this correction angle has its upper and lower limits, which are respectively set to, for example, $\pm10°$ and $\pm20°$.

As described above, according to this embodiment, there is provided an arcuated path which achieves imaging of a target blood vessel from its side at a target position, i.e., a direction in which no shortening occurs. Therefore, the operator can set an optimal imaging angle (working angle) for the blood vessel by simply designating a proper position on the arcuated path.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
an X-ray tube;
an X-ray detector;
a support mechanism which movably supports the X-ray tube and the X-ray detector;
a storage unit which stores data of a three-dimensional model associated with a standard blood vessel structure; and
a control unit which controls the support mechanism on the basis of the three-dimensional model so as to make an imaging central line between the X-ray tube and the X-ray detector become substantially orthogonal to a blood vessel axis of the three-dimensional model.

2. An X-ray diagnostic apparatus comprising:
an X-ray tube;
an X-ray detector;
a support mechanism which movably supports the X-ray tube and the X-ray detector;
a storage unit which stores data of a three-dimensional model associated with a standard blood vessel structure; and
a control unit which controls the support mechanism on the basis of the three-dimensional model so as to limit movement of an imaging central line between the X-ray tube and the X-ray detector within a plane substantially orthogonal to a blood vessel axis of the three-dimensional model.

3. An X-ray diagnostic apparatus comprising:
an X-ray tube;
an X-ray detector;
a support mechanism which movably supports the X-ray tube and the X-ray detector;
a storage unit which stores data of a three-dimensional model associated with a standard blood vessel structure;
a determination unit which determines an arcuated moving path of the X-ray tube centered on a designated position on the basis of the three-dimensional model so as to make an imaging central line between the X-ray tube and the X-ray detector become substantially orthogonal to a blood vessel axis of the three-dimensional model; and
a control unit which controls the support mechanism in accordance with the determined moving path.

4. An apparatus according to claim 3, further comprising a display unit which displays the calculated arcuated moving path together with a human body model.

5. An apparatus according to claim 3, wherein the data of the three-dimensional model is three-dimensional data associated with a human body model.

6. An apparatus according to claim 3, wherein the storage unit stores data of a plurality of three-dimensional models associated with a plurality of blood vessel structures of different regions.

7. An apparatus according to claim 6, wherein in said plurality of three-dimensional models, region names and examination protocol names are associated with each other.

8. An apparatus according to claim 6, wherein said plurality of three-dimensional models are hierarchically classified into large classifications of relatively wide portions of a human body and small classifications of local portions.

9. An apparatus according to claim 8, wherein a plurality of selectable local portions are displayed in accordance with selection among the relatively large portions.

10. An apparatus according to claim 9, wherein the data of the standard three-dimensional model is displayed in accordance with selection among the local portions.

11. An apparatus according to claim 3, further comprising a display unit which displays the calculated arcuated moving path together with an imaging angle corresponding to a designated point on the moving path.

12. An apparatus according to claim 11, further comprising an image generating unit which generates a three-dimensional image corresponding to the imaging angle from the data of the three-dimensional model.

13. An apparatus according to claim 11, wherein the control unit controls the support mechanism in accordance with a designated point on the moving path.

14. An apparatus according to claim 11, wherein the control unit controls the support mechanism so as to move the X-ray tube continuously or intermittently between two points on the calculated arcuated moving path.

15. An apparatus according to claim 3, further comprising a correction unit which corrects a direction of the three-dimensional model so as to reduce a deviation between a coordinate system of the three-dimensional model and an actual subject coordinate system.

16. An apparatus according to claim 15, further comprising a correction angle determination unit which determines a correction angle for the three-dimensional model on the basis of a difference between a branch angle of a blood vessel branch on an actual image associated with the subject and a branch angle on a projection image of the three-dimensional model corresponding to a direction equivalent to an imaging direction of the image.

17. An X-ray diagnostic apparatus comprising:
an X-ray tube;
an X-ray detector;
a support mechanism which movably supports the X-ray tube and the X-ray detector;
a storage unit which stores data of a three-dimensional model associated with a standard blood vessel structure;
a calculation unit which calculates an intersection angle between an imaging central line between the X-ray tube and the X-ray detector and a blood vessel axis of the three-dimensional model; and
a display unit which displays the calculated intersection angle.

18. An imaging position determination device comprising:
a storage unit which stores data of a three-dimensional model associated with a standard blood vessel structure;
a display unit which displays the three-dimensional model;
a setting unit which sets a point of interest on the displayed three-dimensional model in accordance with a user instruction; and
a position determination unit which determines positions of the X-ray tube and X-ray detector such that an imaging central line between the X-ray tube and the X-ray detector becomes substantially orthogonal to a blood vessel axis of the three-dimensional model at the point of interest.

19. A computer-readable storage medium recording a program code for causing a computer to implement
means for displaying data of a three-dimensional model associated with a standard blood vessel structure,
means for setting a point of interest on the displayed three-dimensional model in accordance with a user instruction, and
means for determining positions of an X-ray tube and X-ray detector such that an imaging central line between the X-ray tube and the X-ray detector becomes substantially orthogonal to a blood vessel axis of the three-dimensional model at the point of interest.

20. An imaging position determination method comprising:
displaying data of a three-dimensional model associated with a standard blood vessel structure;
setting a point of interest on the displayed three-dimensional model in accordance with a user instruction; and
determining positions of an X-ray tube and X-ray detector such that an imaging central line between the X-ray tube and the X-ray detector becomes substantially orthogonal to a blood vessel axis of the three-dimensional model at the point of interest.

* * * * *